Dec. 3, 1940. A. F. J. BAUR Plant Pat. 434
CARNATION
Filed June 11, 1940
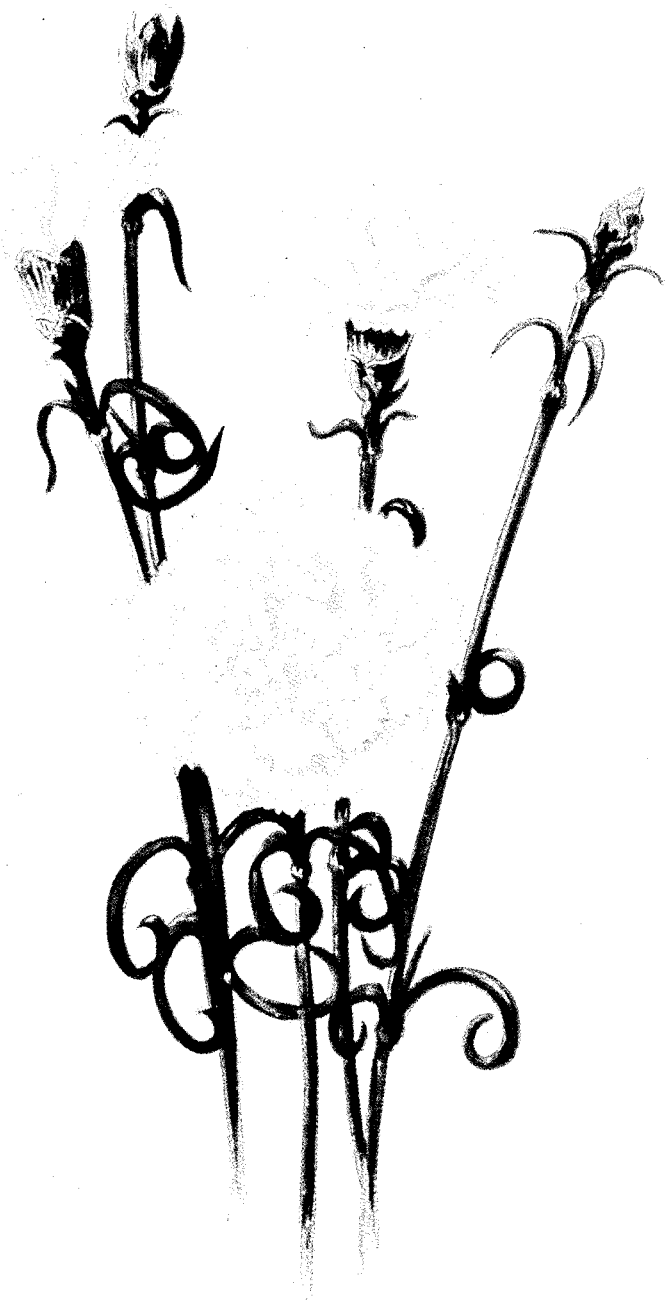
INVENTOR
Adolphe Frederick Jacob Baur
By Orville M. Kile
Plant Patent Agent Patented Dec. 3, 1940

Plant Pat. 434

UNITED STATES PATENT OFFICE

434

CARNATION

Adolphe Frederick Jacob Baur, Indianapolis, Ind., assignor to Baur-Steinkamp and Company, Incorporated, Indianapolis, Ind.

Application June 11, 1940, Serial No. 339,968

1 Claim. (Cl. 47—60)

My present invention relates to improvements in light pink carnations ordinarily known as greenhouse forcing carnations. It is the result of definite breeding in an effort to produce a free flowering pink variety of a grade to compare with the King Cardinal in the red class. A seedling resulting from a self-fertilization of the yellow variety Lucky Strike, was crossed with Light Pink Abundance (Plant Patent No. 56). A seedling resulting from this cross was then crossed with the variety Rosalie (Plant Patent No. 319) and the present variety is one of the resulting seedlings.

This variety has been asexually reproduced and its outstanding characteristics appear to be fixed.

The original illustrations accompanying this application show in full color several specimens of the blossoms of this new variety in various stages of maturity, together with some of the stems and leaves. These are portrayed in approximately the natural colors of the fresh flowers but it must be understood that there may be a slight variation under different growing conditions.

Many of the important distinctive characteristics of this new variety cannot be shown in the illustrations, because of their nature. These outstanding features include the very prolific production of blossoms and the greater length of season in which good quality blossoms are produced; the ease of propagation and the production of unusually good plants in the field—all of which tend to make many more flowers of high quality. Another quality is the tolerance of this variety to fungicidal sprays which makes fungicidal disease control much easier.

Following is a more detailed description of this new variety of carnation. Reference to color plates indicates Ridgway's Color Standards and Nomenclature.

*The plant*

Habits of growth: Upright, vigorous growth. Roots and propagates very readily. Makes unusually good plants in the field.

Blooming habits: Very prolific. Blossoms hold their quality later into the summer than is done by other varieties of similar color.

Disease resistance: Resistant to many diseases common to carnations. Very tolerant of fungicidal sprays.

Foliage: Leaves medium width and fleshy; only slightly curled. Dark Cress Green (Plate XXXI), covered with light gray bloom.

Stems: Strong, sturdy and straight; medium in length; color Dark Dull Yellow Green (Plate XXXII) with lighter nodes. *Nodes*—prominent.

Calyx: Strong, broad, and tough. Seldom splits. Consists of a single tube about 1¼ inches long and ¾ inch wide just below the points. Divided into five lobes, points of which spread to 1¼ inches in width. Color approximately Parrot Green (Plate VI).

Bracts: Strong, appearing in three pairs; approximately the same color as the calyx but with darker tips.

*The flower*

Bud:

*Color.*—Approximately Alzarene Pink (Plate XIII).

*Size.*—Medium.

*Shape.*—Short but not bulged.

Blossom:

*Size.*—Large, from 3½ to 3¾ inches in diameter.

*Form.*—Symmetrical; very full and compact; high-crowned but not all petals extend the same length.

*Petalage.*—Very double. In Indianapolis in April it has from 52 to 58 petals, 6 to 10 of them being very small.

*Fragrance.*—Strong clove fragrance which persists throughout the life of the blossom.

*Longevity.*—Keeps exceedingly well as a cut flower. Blossoms hold their high quality late into the summer.

*Shipping qualities.*—Excellent, particularly because of the good substance of the petals.

*Color.*—The general color effect is approximately Alzarine Pink (Plate XIII), later fading to Venetian Pink (Plate XIII) and Hydrangea Pink (Plate XXVII). It is suffused with an elusive coral glow.

Petals:

*Size.*—Outer petals measure about 1½ inches in width and 2½ inches in length (including the long shank).

*Arrangement.*—Inner petals are considerably folded and curled.

*Edges.*—Serrated and moderately crinkled.

*Substance.*—Extraordinarily good, making blossoms which are very sturdy.

Reproductive organs:

*Stamens.*—Few; white; medium length. *Anthers*—few, large, white. *Filaments*—slender.

*Pistil.*—Usually two-pronged and curled; about 1¾ inches long.

*Ovary.*—Large; high-set; contains many seeds; covers are very tough.

*Comparison*

The known variety most nearly like my new variety is Eleanor, but it differs from that variety principally in the following respects:

1. My new variety produces blossoms which are slightly larger than those of the variety Eleanor.

2. My variety blooms more prolifically.

3. My variety is more tolerant to fungicidal sprays.

4. My variety produces much better plants in the field.

5. The stems of my variety are more moderate in length.

6. The blossoms of my variety are slightly different in color, having an elusive coral glow which is absent in Eleanor.

7. The blossoms of my variety hold their good quality much later in the summer.

8. The blossoms of my variety have petals of much better substance.

Having thus disclosed my invention, I claim:

A new and distinct variety of light pink carnation, characterized particularly by its resistance to disease and tolerance toward fungicidal sprays; its ability to root and transplant easily; the ability of its blossoms to hold their high quality late into the summer; and its prolific production of blossoms of large size, symmetrical form, exceptionally good substance, strong clove fragrance, and color which is substantially as shown and described.

ADOLPHE FREDERICK JACOB BAUR.